United States Patent [19]
Hungate et al.

[11] Patent Number: 5,811,462
[45] Date of Patent: Sep. 22, 1998

[54] HIV PROTEASE INHIBITORS USEFUL FOR THE TREATMENT OF AIDS

[75] Inventors: Randall W. Hungate, Lansdale; Joseph P. Vacca, Telford, both of Pa.; Byeong Moon Kim, Seoul, Rep. of Korea

[73] Assignee: Merck & Co., Inc., Rahway, N.J.

[21] Appl. No.: 850,360

[22] Filed: May 2, 1997

Related U.S. Application Data

[60] Provisional application No. 60/016,685 May 2, 1996.

[51] Int. Cl.$^6$ .................. A61K 31/16; C07D 233/60; C07D 307/93
[52] U.S. Cl. .................. 514/616; 514/265.5; 514/255; 514/468; 564/152; 564/153; 549/300; 544/141; 544/360; 544/389; 544/390
[58] Field of Search .................. 564/152, 153; 514/616, 235.5, 255, 468; 544/141, 360, 389, 390; 549/300

[56] References Cited

U.S. PATENT DOCUMENTS 5,413,999  5/1995  Vacca et al. .................. 514/231.5

FOREIGN PATENT DOCUMENTS

| 0337714 | 10/1989 | European Pat. Off. . |
|---|---|---|
| 0356223A | 2/1990 | European Pat. Off. . |
| 0434365A | 6/1991 | European Pat. Off. . |
| 0487270 | 5/1992 | European Pat. Off. . |
| 0550924 | 7/1993 | European Pat. Off. . |

*Primary Examiner*—Joseph K. McKane
*Attorney, Agent, or Firm*—Melvin Winokur; Kenneth R. Walton

[57] ABSTRACT

Peptide analogs containing norbornene are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

9 Claims, No Drawings

HIV PROTEASE INHIBITORS USEFUL FOR THE TREATMENT OF AIDS

This application claims the priority of provisional application Ser. No. 60/016,685 filed May 2, 1996.

This application is related to U.S. Pat. No. 5,413,999, Merck Case 18416, EPO 550924.

The present invention is concerned with compounds which inhibit the protease encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277(1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. Applicants demonstrate that the compounds of this invention are inhibitors of HIV protease.

Applicants have discovered that norbornene derivatives of peptide analogs are potent HIV protease inhibitors.

BRIEF DESCRIPTION OF THE INVENTION

Compounds of Formulas I or II, as herein defined, are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

Some abbreviations that may appear in this application are as follows.

| | Activating Group |
|---|---|
| HBT(HOBT or HOBt) | 1-hydroxybenzotriazole hydrate |
| Designation | Coupling Reagent |
| EDC | 1-ethyl-3-(3-dimethylaminopropyl) carbodiimide hydrochloride |
| | Other |
| DMF | dimethylformamide |
| Et$_3$N | triethylamine |
| EtOAc | ethyl acetate |

DETAILED DESCRIPTION OF THE INVENTION AND PREFERRED EMBODIMENTS

This invention is concerned with compounds of Formulas I or II, combinations thereof, or pharmaceutically acceptable salts thereof, in the inhibition of HIV protease, the prevention or treatment of infection by HIV and in the treatment of the resulting acquired immune deficiency syndrome (AIDS). Compounds of Formulas I or II are defined as follows:

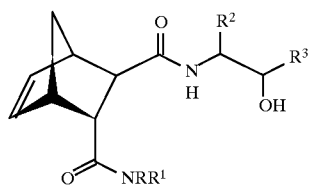

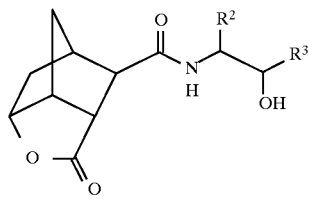

R and $R^1$ are independently
a) hydrogen, or
b) —$C_{1-4}$alkyl unsubstituted or substituted with one or more of
  i) halo,
  ii) hydroxy,
  iii) $C_{1-3}$ alkoxy,
  iv) aryl unsubstituted or substituted with one or more of $C_{1-4}$alkyl, $C_{1-4}$alkoxy, nitro, amino, amido, carboxy, hydroxy, halo or aryl;
  v) —W-aryl or W-benzyl, wherein W is —O—, —S—, or —NH—; or
  vii) heterocycle, unsubstituted or substituted with one or more of $C_{1-4}$alkyl, hydroxy or halo;
  viii) carboxyl;
c) —$C_{3-5}$cycloalkyl, unsubstituted or substituted at the 3-position with $C_{1-4}$alkyl;
d) aryl unsubstituted or substituted with halo, $C_{1-4}$ alkyl unsubstituted or substituted one or more times with hydroxy; or
e) R and $R^1$ are joined together to form a 4–6 membered cycloalkyl or a heterocycle; and $R^2$ is
a) hydrogen;

b) Phenyl unsubstituted or substituted with one or more of —OH or $C_{1-3}$ alkoxy;
c) $C_{5-7}$cycloalkyl, unsubstituted or substituted with one or more of —OH or $C_{1-3}$alkoxy; or
d) $C_{1-4}$ alkyl; and $R^3$ is —$CH_2NR^5R^6$, or

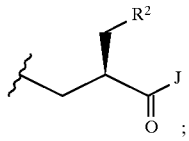

and
$R^4$ is
a) a 5- to 7-membered heterocycle, which heterocycle is unsubstituted or substituted with one or more of —$C_{1-4}$alkyl, oxo, amino or halo;
b) aryl unsubstituted or substituted with one or more of —$C_{1-4}$alkyl, $C_{1-4}$ alkoxy, nitro, oxo, amino, amido, carboxy, hydroxy, halo, or aryl;
c) $C_{1-4}$alkyl, unsubstituted or substituted once with aryl or 5- to 7-membered heterocycle; or
d) $C_{3-5}$cycloalkyl, unsubstituted or substituted at the 3-position with $C_{1-4}$alkyl; and $R^5$ is
a) —V—$R^4$; wherein V is —C(O)—Q—, or —$SO_2$— Q—, wherein Q is absent, —O—, or —NH—; and $R^6$ is
a) hydrogen, or
b) —$C_{1-4}$alkyl unsubstituted or substituted with one or more of
  i) halo,
  ii) hydroxy,
  iii) $C_{1-3}$alkoxy,
  iv) aryl unsubstituted or substituted with one or more of $C_{1-4}$alkyl, $C_{1-4}$alkoxy, nitro, amino, amido, carboxy, hydroxy, halo or aryl;
  v) —W-aryl or W-benzyl, wherein W is —O—, —S—, or —NH—; or
  vi) heterocycle, unsubstituted or substituted with one or more of $C_{1-4}$alkyl, hydroxy or halo;
  vii) carboxyl;
c) —$C_{3-5}$cycloalkyl, unsubstituted or substituted at the 3-position with $C_{1-4}$alkyl; or
d) aryl unsubstituted or substituted with one or more of $C_{1-4}$alkyl, $C_{1-4}$alkoxy, nitro, amino, amido, carboxy, hydroxy, halo or aryl; and J is

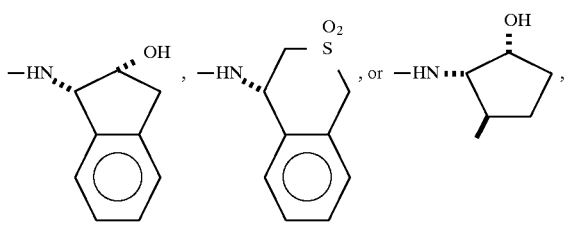

or pharmaceutically acceptable salts thereof.

Preferred compounds of the present invention include the following:

Compound A

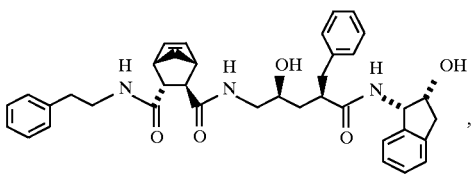

Compound B

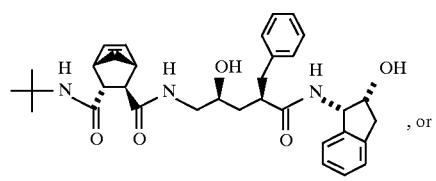

Compound C

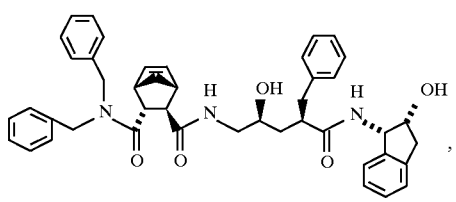

or pharmaceutically acceptable salts thereof.

The compounds of the present invention, may have asymmetric centers and occur as racemates, racemic mixtures and as individual diastereomers, or enantiomers with all isomeric forms being included in the present invention.

When any variable (e.g., aryl, heterocycle, R, $R^1$, $R^2$, etc.) occurs more than one time in any constituent or in Formulas I or II, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; and "cycloalkyl" is intended to include saturated ring groups, such as cyclopropyl, cyclobutyl, cyclopentyl, cyclohexyl (Cyh) and cycloheptyl. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable salts of the compounds of Formulas I or II (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes 1–6 for preparing the novel compounds of this invention are presented below. The Schemes are not limited by any particular substituents employed in the schemes for illustrative purposes. The examples specifically illustrate the application of the following schemes to specific compounds.

Amide couplings used to form the compounds of this invention are typically performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Additional related information on synthetic background is contained in EPO 0337714.

Scheme I illustrates one method of synthesizing the compounds of the present invention, particularly when the $NRR^1$ group forms morpholine. The dicarboxylate 1 is coupled to morpholine in the presence of the peptide coupling reagent EDC to give 2. Subsequent reaction with DBU gives 3, which ester is converted to the carboxylic acid 4 by reaction with base. Coupling of 4 with 5 (prepared in EP 550924) with EDC gives 6.

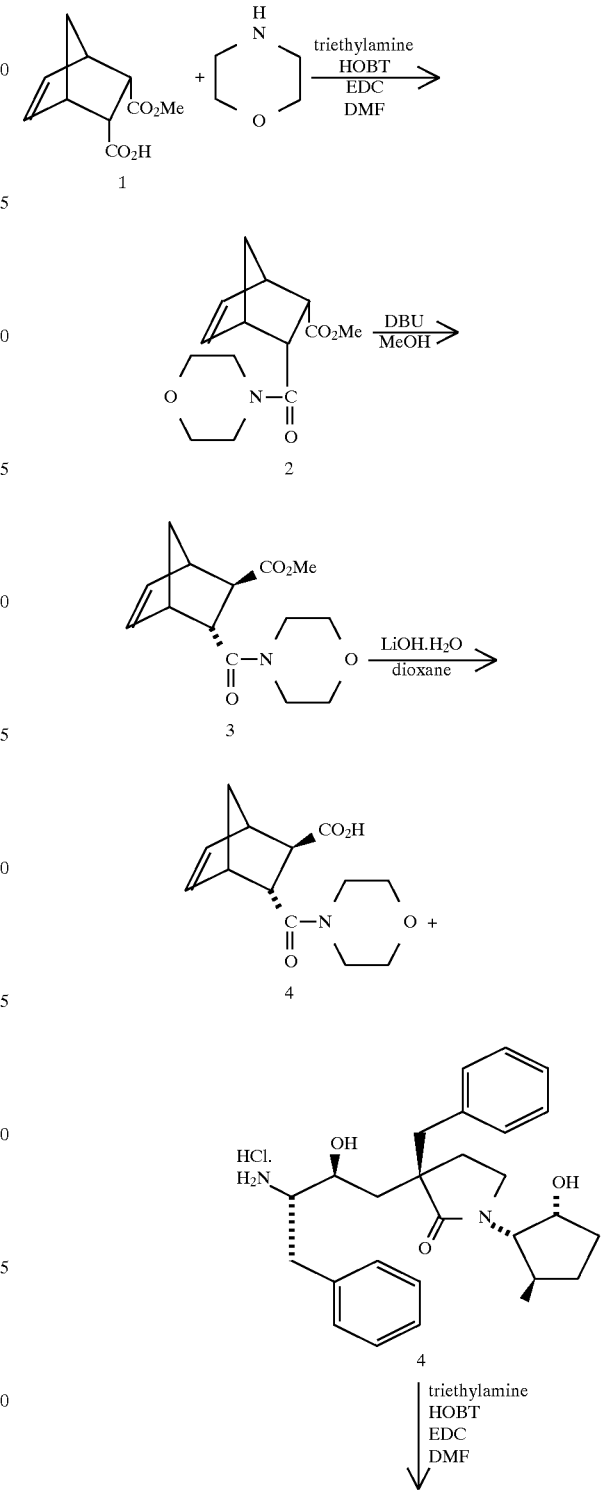

SCHEME 1

-continued
SCHEME 1

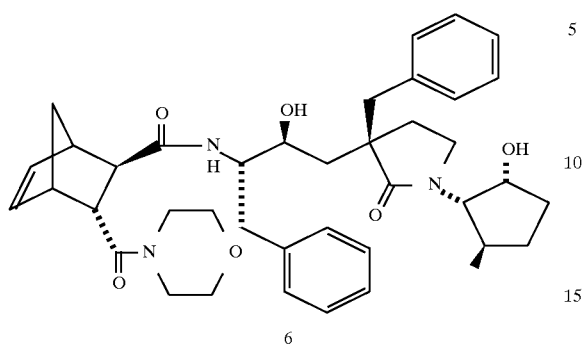

6

Synthesis of enantiomerically pure, various amide substituted, norbornenyl carboxylic acids (6) is also outlined in Scheme 2. The iodolactone 7 was prepared according to the procedure of Hamanaka et al. (N. Hamanaka, T. Seko, T. Miyazaki, M. Naka, K. Furuta and H. Yamamoto, *Tetrahedron Lett.* 1989, 30, 2399–2402). Compound 7 was esterified to the ethyl ester 8 by heating with a catalytic amount of conc $H_2SO_4$ in ethyl alcohol. Treatment of 8 with zinc in acetic acid provided Compound 9. The acid moiety in Compound 9 was converted to the corresponding acid chloride (10) and the acid chloride was subsequently coupled to various amines to provide amide 11. The ethyl ester moiety in Compound 11 was hydrolyzed to the corresponding acid 12 by treating with LiOH in DME-water.

SCHEME 2

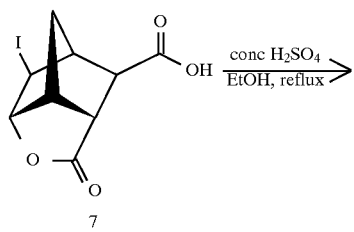

7

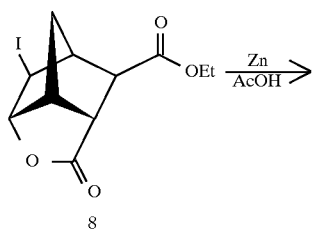

8

-continued
SCHEME 2

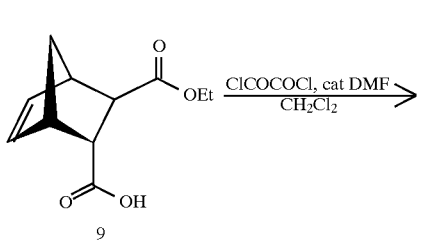

9

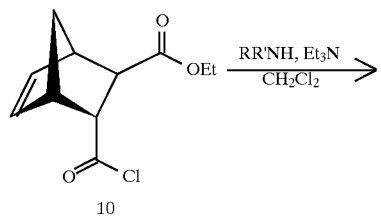

10

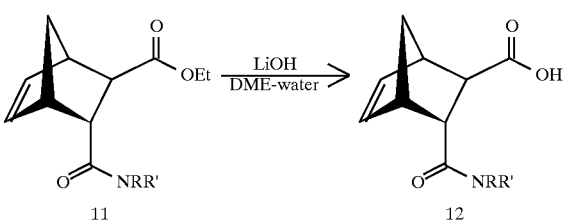

11    12

Scheme 3 shows the preparation of the piperazine side of the inhibitor molecules for the norbornene-hydroxyethylpiperazine class of inhibitors. Reaction of Compound 13 (D. Askin, K. K. Eng, K. Rossen, R. M. Purick, K. M. Wells, R. P. Volante, and P. J. Reider, *Tetrahedron Lett.* 1994, 35, 673–676) with (S)-glycidyl m-nitrophenyl-sulfonate in the presence of diisopropylethylamine provided the epoxide 15. Opening of the epoxide moiety in Compound 15 with $LiN_3$ in isopropanol gave Compound 16. Reduction of Compound 16 under hydrogen atmosphere in presence of Pd catalyst provided free amine 17.

SCHEME 3
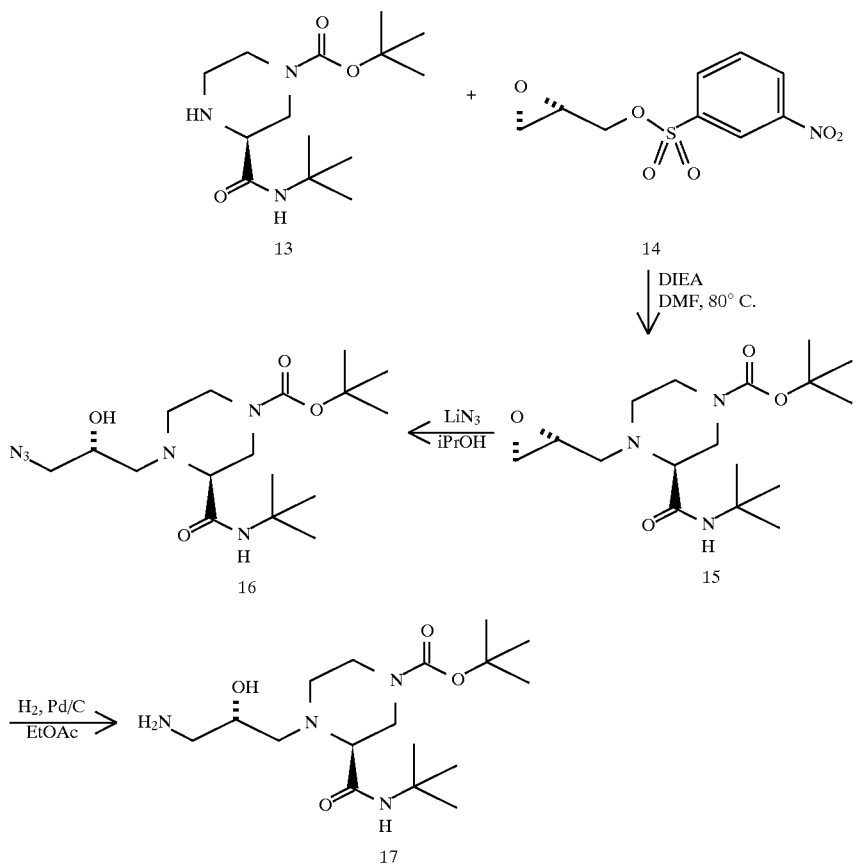
The Compound 12 and 17 were coupled under peptide coupling conditions using HOBT, EDC and triethylamine in DMF to give the Compound 18 as shown in Scheme 4. Compound 18 was treated with gaseous HCl to deprotect the Boc group and free amine 19 was generated. Preparation of substituted Compounds such as 20 or 21 was accomplished as shown in Scheme 4.
SCHEME 4
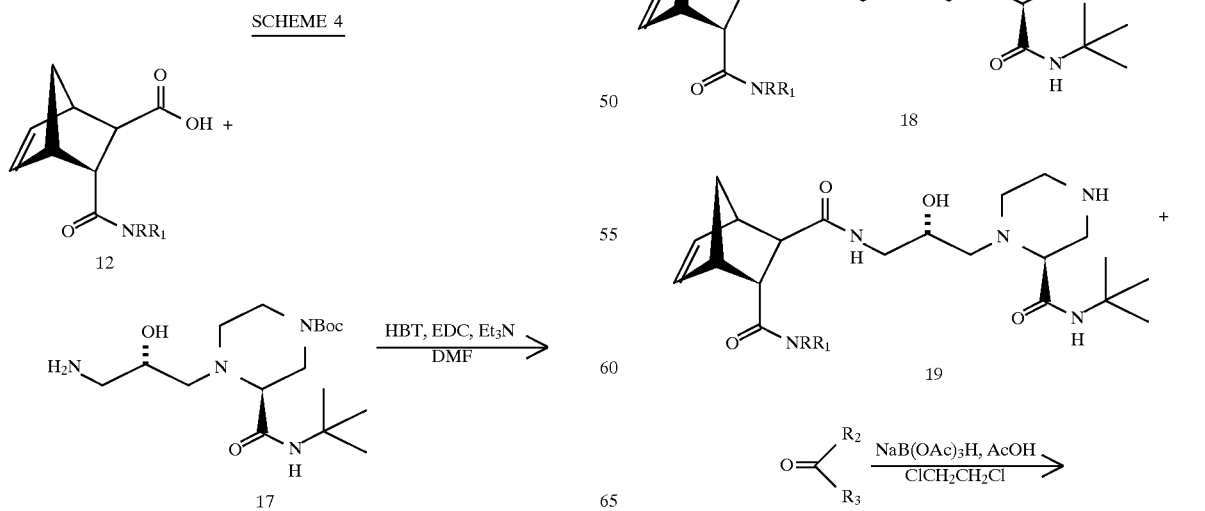

-continued
SCHEME 4

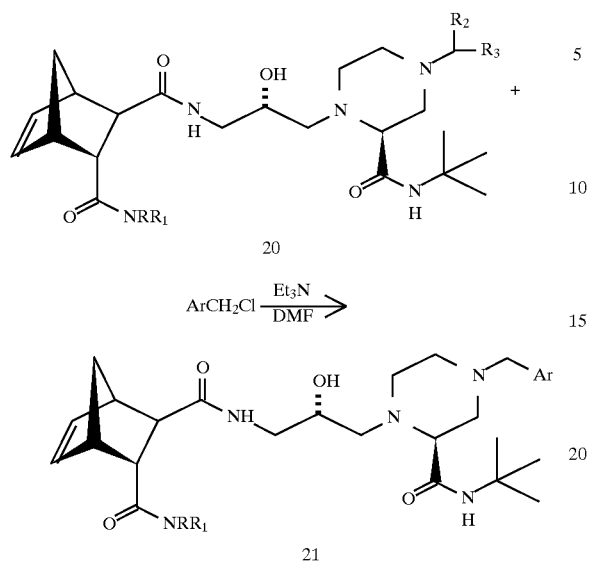

20

ArCH₂Cl $\xrightarrow{\text{Et}_3\text{N}}{\text{DMF}}$

21

Scheme 5 shows the synthesis of the norbornene-hydroxyethylsulfonamide class of inhibitors. Isobutylamine was coupled to arenesulfonyl chloride to give Compound 22. The sulfonamide group of Compound 22 was alkylated by first deprotonating with nBuLi followed by addition of proper alkylating agent such as epichlorohydrin. The epoxide moiety in Compound 23 was opened by an azide group and the corresponding azidoalcohol (Compound 24) was reduced to the amine 25. The amine 25 was then coupled to norbornenyl acid (Compound 12) using HOBT and EDC as coupling reagents to furnish Compound 26. Various amides at the norbornenyl side chain were prepared.

SCHEME 5

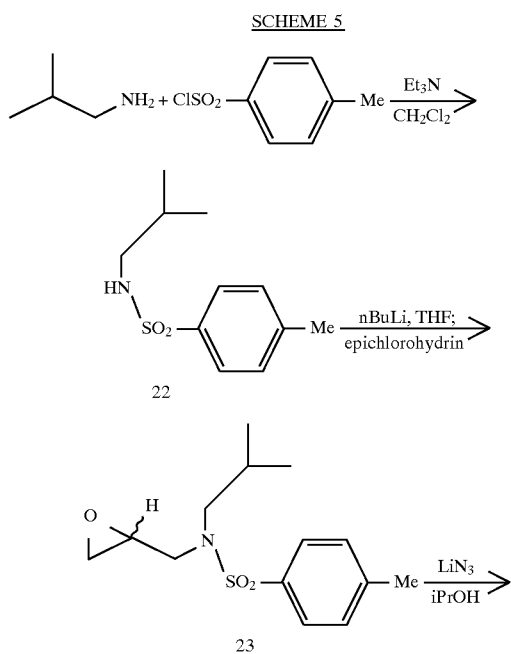

-continued
SCHEME 5

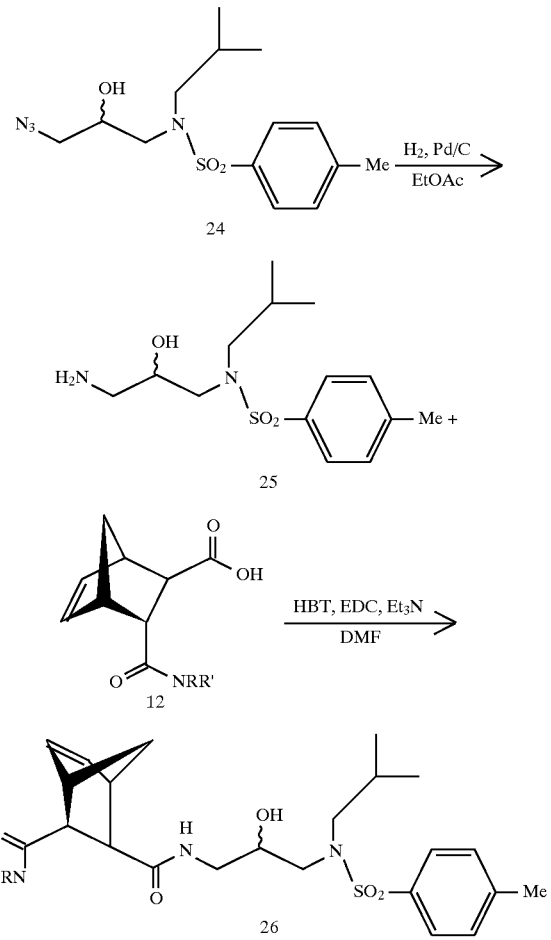

Scheme 6 delineates a general synthesis of norbornene-pentanamide class of inhibitors. The epoxide 27 (D. Askin, K. K. Eng, K. Rossen, R. M. Purick, K. M. Wells, R. P. Volante, and P. J. Reider, *Tetrahedron Lett.* 1994, 35, 673–676) was opened with LiN₃ by heating in isopropanol to give azidoalcohol 28. The azide moiety was reduced to the corresponding amine by the use of a Pd catalyst under hydrogen atmosphere to yield Compound 29. The protecting group of Compound 29 was removed by passing gaseous HCl through to give Compound 30. Compound 30 was then coupled to acid 12 under HOBT and EDC coupling conditions to furnish Compound 31. Various amides at the norbornenyl side chain were prepared.

SCHEME 6

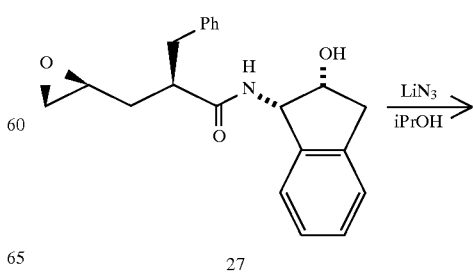

27

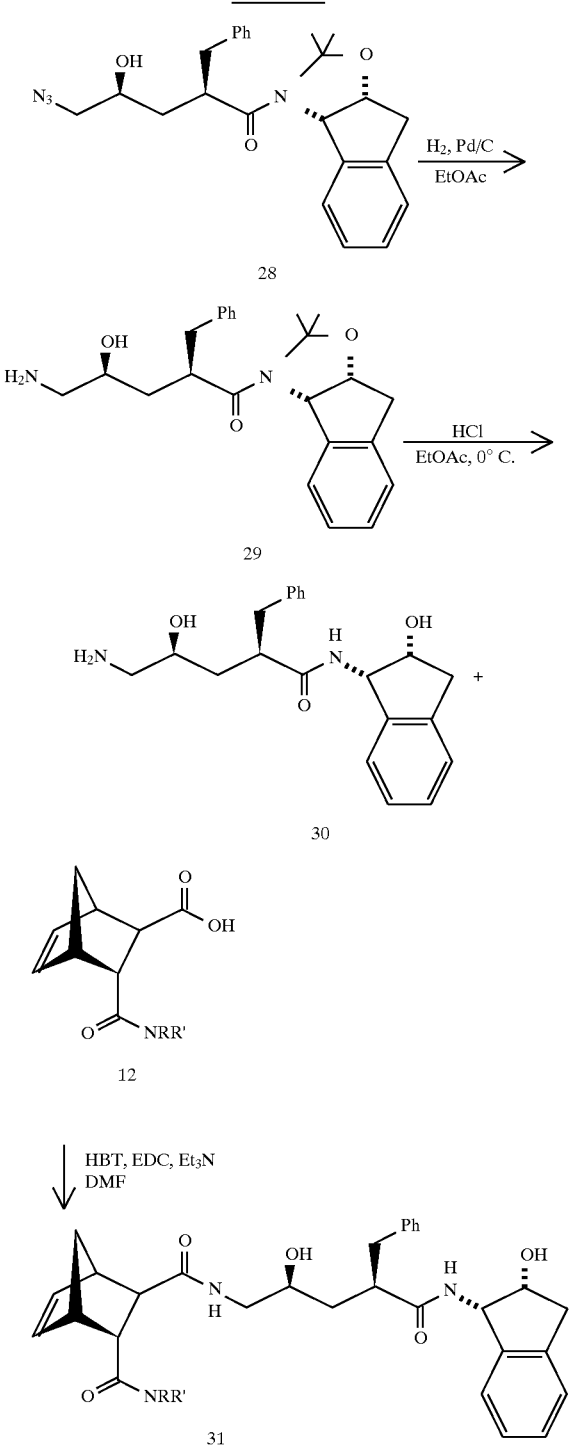

-continued
SCHEME 6

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. | AIDS, ARC, HIV |

TABLE C-continued

| Drug Name | Manufacturer | Indication |
|---|---|---|
| | Ind. Ltd. (Osaka, Japan) | positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| IMMUNO-MODULATORS | | |
| AS-101 | Wyeth-Ayerst Labs. (Philadelphia, PA) | AIDS |
| Bropirimine | Upjohn (Kalarnazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | MDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |

TABLE C-continued

| Drug Name | Manufacturer | Indication |
| --- | --- | --- |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

The synthesis of ddC, ddI and AZT are also described in EPO 484071.

Preferred combinations are simultaneous or alternating treatments of an inhibitor of HIV protease and a nucleoside inhibitor of HIV reverse transcriptase, such as AZT, ddC or ddI. Preferred inhibitors of HIV protease are Compounds A–D, most preferred are compounds E and F.

Assay for Inhibition of Microbial Expressed HIV Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 µl DMSO were added to 25 µl of the peptide solution in water. The reaction is initiated by the addition of 15 µl of 0.33 nM protease (0.11 ng) in a solution of 0.133M Na acetate pH 5.5 and 0.1% bovine serum albumin. The reaction was quenched with 160 µl of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compounds A–C showed $IC_{50}$ values as provided in the Table.

TABLE

| Compound | $IC_{50}$ (nM) |
| --- | --- |
| A | 0.055 |
| B | 82.8 |
| C | 0.025 |

EXAMPLE 1

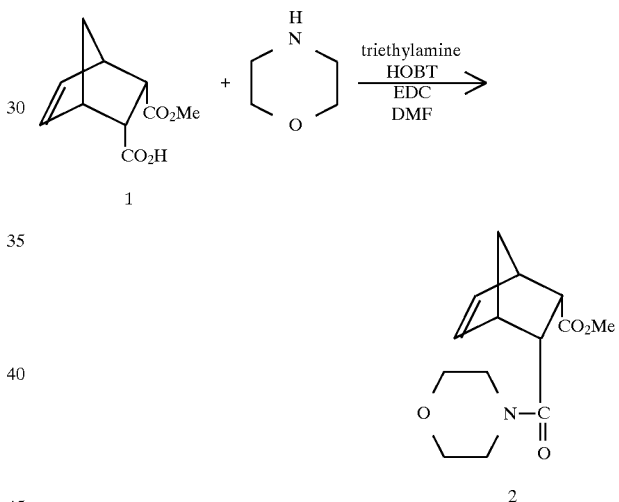

Synthesis of racemic cis-methyl-3-(morpholinyl) carbonyl bicyclo-(2.2.1.)hept-5-ene-2-carboxylate, Compound 2

To a stirred solution of methyl cis-5-norbornene-endo-2, 3-dicarboxylate 1 (3.00 g, 15.3 mmol) in dimethylformamide (30 mL) was added triethylamine (1.85 g, 2.55 mL, 18.3 mmol), 1-hydroxy-benzotriazole hydrate (2.47 g, 18.3 mmol), 1-(3-dimethylaminopropyl)-3-ethylcarbodiimide hydrochloride (3.51 g, 18.3 mmol), and morpholine (1.59 g, 1.60 mL, 18.3 mmol). The solution was stirred at room temperature for 16 h. The solution was concentrated, diluted with ethyl acetate, and washed with saturated $NaHCO_3$ (2×25 mL) and brine (1×25 mL). The organic layer was dried ($Na_2SO_4$) and concentrated to give 2 (4.01 g) as a crude oil which was used without further purification. Partial $^1H$ NMR ($CDCl_3$, 300 MHz) δ in ppm: 6.80 (m,1H), 6.30 (m,1H), 3.57 (m, 8H), 3.60 (s, 3H), 3.34 (dd, 1H), 3.30 (dd,1H), 3.20 (bs, 1H), 3.10 (bs, 1H), 1.47 (m, 1H), 1.35 (d, 1H).

EXAMPLE 2

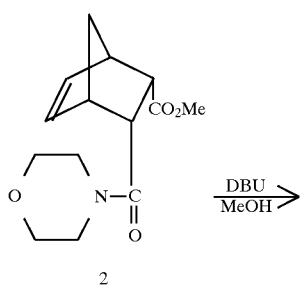

Synthesis of racemic trans-methyl-3-(morpholinyl) carbonyl bicyclo-(2.2.1.)hept-5-ene-2-carboxylate, Compound 3

To a stirred solution of 2 in methanol (14 mL) was added 1,8-diazabicyclo[5.4.0]undec-7-ene (3.29 g, 3.23 mL, 21.6 mmol). The solution was heated at reflux for 16 h. The solution was cooled to room temperature, concentrated, diluted with ethyl acetate, and washed with 1N HCl (2×25 mL). The organic layer was dried ($Na_2SO_4$) and concentrated to give 3 (2.9 g) as a crude oil which was used without further purification. Partial $^1$H NMR ($CDCl_3$, 400 MHz) δ in ppm: 6.28 (m, 1H), 5.95 (m, 1H), 3.61 (m, 7H), 3.65 (s, 3H), 3.44 (m, 1H), 3.10 (dd, 1H), 3.04 (s, 1H), 2.93 (dd, 1H), 2.024 (t, 1H), 1.61 (d, 1H), 1.42 (dd, 1H).

EXAMPLE 3

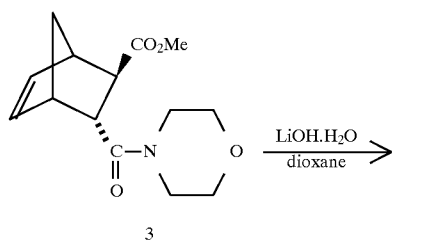

Synthesis of racemic trans-3-(morpholinyl) carbonyl bicyclo(2.2.1.)-hept-5-ene-2-carboxylate, Compound 4

Lithium hydroxide monohydrate (906 mg, 21.6 mmol) was added to a solution of 3 in dioxane (20 mL). The solution was stirred at room temperature for 16 h. The solution was concentrated, diluted with ethyl acetate, and washed with 1N HCl (2×25 mL). The organic layer was dried ($Na_2SO_4$) and concentrated to give 4 (2.5 g) as a white solid which was used crude. Partial $^1$H NMR ($CDCl_3$, 400 MHz) δ in ppm: 6.32 (dd, 1H), 5.97 (dd, 1H), 3.64 (m, 8H), 3.46 (m, 1H), 3.20 (s, 1H), 3.07 (s, 1H), 2.99 (m, 1H), 2.07 (s, 1H), 1.61 (m, 1H), 1.45 (m, 1H).

EXAMPLE 4

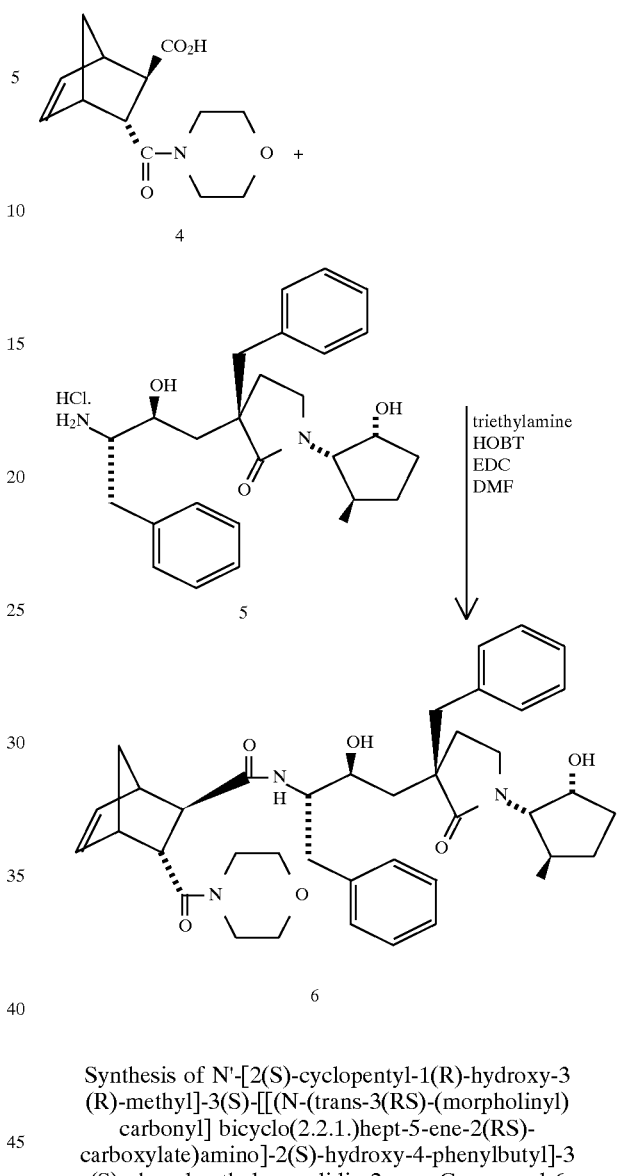

Synthesis of N'-[2(S)-cyclopentyl-1(R)-hydroxy-3 (R)-methyl]-3(S)-[[(N-(trans-3(RS)-(morpholinyl) carbonyl] bicyclo(2.2.1.)hept-5-ene-2(RS)-carboxylate)amino]-2(S)-hydroxy-4-phenylbutyl]-3 (S)-phenylmethyl-pyrrolidin-2-one, Compound 6

To a stirred solution of 4 (500 mg, 1.99 mmol) in dimethylformamide (6 mL) was added triethylamine (443 mg, 0.663 mL, 4.38 mmol), 1-hydroxybenzotriazole hydrate (322 mg, 2.38 mmol), 1-(3-dimethylaminopropyl)-3-ethylcarbodiimide hydrochloride (456 mg, 2.38 mmol), and 5 (prepared as described in EPO 550924) (913 mg, 1.99 mmol). The solution was stirred at room temperature for 7 h. The solution was concentrated, diluted with ethyl acetate, and washed with saturated $NaHCO_3$ (2×25 mL), and brine (1×25 mL). The organic layer was dried ($Na_2SO_4$) and concentrated. The resulting white solid was purified by flash chromatography (10% hexane/ethyl acetate) to give the less polar single diastereomer of 6 (70 mg), mixture of diastereomers of 6 (875 mg), and the more polar single diastereomer of 6 (85 mg), all as white solids. Less polar, single diastereomer of 6: MP=103°–106° C., partial $^1$H NMR ($CDCl_3$, 400 MHz) δ in ppm: 7.23 (m, 10H), 6.36 (s, 1H), 6.28 (dd, 1H), 6.17 (d, 1H), 6.08 (dd, 1H), 4.09 (m, 3H), 3.53 (m, 8H), 3.37 (t, 1H), 3.17 (m, 2H), 2.94 (m, 4H), 2.72 (m, 1H), 2.64 (d, 1H), 2.57 (d, 1H), 2.18 (m, 2H), 1.99 (m, 2H), 1.88 (d, 1H), 1.78 (m, 2H), 1.51 (m, 3H), 1.36 (bd, 1H), 1.11 (m, 1H), 0.901 (d, 3H), 0.690 (s, 1H). Mixture of diastereomers of 6: MP=102°–104° C. More polar, single diastereomer of 6: MP=101°–104° C., partial $^1$H NMR (CDCl$_3$, 400 MHz) δ in ppm: 7.25 (m, 10H), 6.41 (s, 1H), 6.28 (dd, 1H), 6.15 (d, 1H), 6.02 (dd, 1H), 4.11 (m, 3H), 3.63 (m, 8H), 3.48 (dd, 1H), 3.16 (m, 2H), 2.96 (m, 4H), 2.71 (m, 2H), 2.55 (d, 1H), 2.17 (m, 2H), 1.89 (m, 5H), 1.50 (m, 3H), 1.28 (d, 1H), 1.11 (m, 1H), 0.926 (d, 3H), 0.683 (s, 1H).

EXAMPLE 5

Preparation of 4(R)-Ethoxycarbonyl-6(S)-iodo-2-oxo-3(R),5(S),7(S),-8(S)-1-oxatricyclo[3.2.1.1$^{5.8}$] nonane, Compound 8

To Compound 7 (3.766 g, 12.2 mmol) in absolute ethanol (21 mL) was added 3 drops of conc sulfuric acid and the mixture was heated to reflux for 15 h. The solvent was removed and the residue was dissolved in ethyl acetate, washed with sat aq NaHCO$_3$ solution and brine, and the organic solution was dried over anhyd MgSO$_4$. Filtration and evaporation of the solvent provided a light yellow oil (3.897 g, 95% yield). $^1$H NMR (CDCl$_3$) 1.28 (3H, t, J=7.1 Hz), 1.98 (1H, d, J=11.9 Hz), 2.33 (1H, d, J=11.9 Hz), 2.83 (1H, br s), 3.02 (1H, br s), 3.11 (1H, m), 3.20 (1H, m), 3.89 (1H, d, J=2.4 Hz), 4.19 (2H, q, J=7.1 Hz), 5.14 (1H, J=4.9 Hz)

EXAMPLE 6

Preparation of 3(R)-Ethoxycarbonyl-1(S),4(R)-bicyclo-[2.2.1]hept-5-en-2(R)-yl carboxylic acid, Compound 9

To a magnetically stirred solution of Compound 8 (3.897 g, 11.6 mmol) in acetic acid (25 mL) was added zinc dust (Aldrich, 7.58 g, 116 mmol). The mixture was heated at 60° C. while stirring for 4 h. The mixture was cooled to room temperature, and concentrated under reduced pressure. The residue was taken up in EtOAc (100 mL) and washed with water (2×50 mL) and brine (50 mL). The aqueous layer was extracted with EtOAc(10×30 mL). Combined organic solution was dried over anhyd MgSO$_4$ and concentrated in vacuo to yield 2.507 g of a pale yellow oil (100% yield). $^1$H NMR (CDCl$_3$) 1.28 (3H, t, J=7.1 Hz), 1.48 (1H, dd, J=8.8, 1.6 Hz), 1.63 (1H, d, J=8.8 Hz), 2.10 (1H, s), 2.64 (1H, dd, J=4.6, 1.5 Hz), 3.14 (1H, d, J=0.7 Hz), 3.30 (1H, s), 3.44 (1H, dd, J=4.2, 4.0 Hz), 4.18 (2H, q, J=7.1 Hz), 6.14 (1H, dd, J=5.5, 2.8 Hz), 6.30 (1H, dd, J=5.5, 3.1 Hz)

EXAMPLE 7

Preparation of N-2'-Phenylethyl 3(R)-Ethoxycarbonyl-1(S),4(R)-bicyclo[2.2.1]hept-5-en-2(R)-yl carboxamide, Compound 11 (RR$_1$=H, CH$_2$CH$_2$Ph)

To a magnetically stirred solution of Compound 9 (500 mg, 2.38 mmol) in CH$_2$Cl$_2$ (5 mL) were added oxalyl chloride (0.25 mL, 2.85 mmol) and N,N-dimethylformamide (9 μL, 0.119 mmol) at 0° C. This mixture was stirred for 18 h while allowing to warm to room temperature. Solvent was removed under reduced pressure and the reside was dissolved in dry CH$_2$Cl$_2$ (6 mL). To this solution were added triethylamine (0.66 mL, 4.76 mmol), phenylethylamine (0.45 mL, 3.57 mmol) and DMAP (20 mg). The mixture was stirred for 18 h at room temperature. More CH$_2$Cl$_2$ (10 mL) was added and the solution was washed with 1N aq HCl solution (10 mL), water (5 mL), sat aq NaHCO$_3$ (5 mL) and brine (5 mL). Drying over anhyd MgSO$_4$ followed by concentration provided a brownish oil (0.510 g, 69% yield). $^1$H NMR (CDCl$_3$) 1.24 (3H, t, J=7.1 Hz), 1.44 (1H, dd, J=8.6, 1.5 Hz), 1.52 (1H, d, J=8.8 Hz), 2.48 (1H, d, J=2.6 Hz), 2.79 (2H, t, J=6.9 Hz), 3.07 (2H, d, J=3.3 Hz), 3.12 (1H, d, J=1.3 Hz), 3.46 (2H, m), 4.14 (2H, q, J=7.1 Hz), 5.80 (1H, br s), 6.12 (1H, dd, J=5.5, 2.0 Hz), 6.22 (1H, dd, J=5.7, 3.1 Hz), 7.17–7.32 (5H, m).

EXAMPLE 8

Preparation of N,N-bis(2'-Phenylethyl) 3(R)-Ethoxycarbonyl-1(S),-4(R)-bicyclo[2.2.1]hept-5-en-2(R)-yl carboxamide, Compound 11 (RR$_1$= (CH$_2$PH)$_2$)

Same procedure as above for Compound 11 (RR$_1$=H, CH$_2$CH$_2$Ph).

$^1$H NMR (CDCl$_3$) 1.22 (3H, t, J=7.2 Hz), 1.44 (1H, dd, J=8.8, 1.6 Hz), 1.57 (1H, d, J=8.8 Hz), 3.05 (1H, dd, J=4.6, 1.5 Hz), 3.08 (1H, s), 3.19 (1H, s), 3.63 (1H, dd, J=4.6, 3.3 Hz), 4.09 (2H, m), 4.16 (1H, d, J=14.8 Hz), 4.44 (1H, d, J=16.5 Hz), 4.79 (1H, d, J=17.0 Hz), 4.90 (1H, d, J=14.8 Hz), 6.08 (1H, dd, J=5.5, 2.9 Hz), 6.39 (1H, dd, J=5.5, 3.1 Hz), 7.14–7.38 (5H, m)

EXAMPLE 9

Preparation of 3(R)-(N-2'-Phenylethyl) amidocarboxy-1(R),4(S)-bicyclo[2.2.1]hept-5-en-2(R)-yl carboxylic acid, Compound 12 (RR$_1$=H, CH$_2$CH$_2$Ph)

To a magnetically stirred solution of Compound 11 (RR'=H, CH$_2$CH$_2$Ph, 510 mg, 1.628 mmol) in DME (10 mL) and water (10 mL) was added LiOH.H$_2$O (0.342 g, 8.14 mmol) and the mixture was stirred for 60 h at ambient temperature. The volume of the solvent was reduced to ~a third by rotary evaporation and conc HCl was added to adjust pH of the mixture to 2–3. The aqueous solution was extracted with EtOAC (10×20 mL) and the organic layer was dried over anhyd MgSO$_4$. Filtration followed by concentration provided 0.411 g (88% yield) of a pale brown solid. $^1$H NMR (CDCl$_3$) 1.56 (2H, d, J=0.9 Hz), 2.44 (1H, d, J=5.9 Hz), 2.83 (2H, t, J=6.8 Hz), 3.01 (1H, s), 3.02 (1H, m), 3.19 (1H, s), 3.48 (1H, m), 3.59 (1H, m), 5.66 (1H, br s), 5.92 (1H, dd, J=5.3, 2.4 Hz), 6.29 (1H, dd, J=5.7, 3.3 Hz), 7.16–7.35 (5H, m).

EXAMPLE 10

Preparation of N,N-bis(2'-Phenylethyl) amidocarboxy-1(R),4(S)-bicyclo[2.2.1]hept-5-en-2(R)-yl carboxylic acid, Compound 12 (RR$_1$= (CH$_2$Ph)$_2$)

Same procedure as above for Compound 12 (RR$_1$=H, CH$_2$CH$_2$Ph).

$^1$H NMR (CDCl$_3$) 1.48 (1H, dd, J=8.8, 1.6 Hz), 1.58 (1H, d, J=8.8 Hz), 3.10 (1H, s), 3.15 (1H, dd, J=4.6, 1.3 Hz), 3.26 (1H, d, J=1.5 Hz), 3.64 (1H, dd, J=4.1, 3.7 Hz), 4.21 (1H, d, J=14.7 Hz), 4.21 (1H, d, J=16.9 Hz), 4.79 (1H, d, J=16.7 Hz), 4.87 (1H, d, J=16.7 Hz), 6.07 (1H, dd, J=5.5, 2.9 Hz), 6.42 (1H, dd, J=5.7, 3.3 Hz), 7.15–7.39 (10H, m)

EXAMPLE 11

Preparation of N-tert-butyl 1-(2'(S),3'-epoxypropyl)-4-tert-butyloxy-carbonylpiperazine-2(S)-carboxamide, Compound 15

To a magnetically stirred solution of Compound 13 (5.225 g, 18.31 mmol) and Compound 14 (4.746 g, 18.31 mmol) in DMF (35 mL) was added DIEA (3.508 mL, 20.14 mmol). The mixture was heated to 80° C. initially and kept at 65° C. for 7 h. Then the mixture was stirred at room temperature for 15 h. Sat aq NaHCO₃ solution (35 mL) was added and the mixture was stirred at 50° C. for 0.5 h. After cooling to room temperature, EtOAc (300 mL) was added and the organic solution was extracted with water (50 mL×3) and brine (50 mL). The organic layer was dried over anhyd Na₂SO₄, filtered, and concentrated by rotary evaporation. The residue was purified on a silica gel chromatographic column to provide 4.708 g of a pale yellow solid (75% yield). ¹H NMR (CDCl₃) 1.36 (9H, s), 1.45 (9H, s), 2.17 (1H, m), 2.28 (1H, dt, J=3.3, 11.7 Hz), 2.56 (1H, m), 2.76 (1H, dd, J=10.3, 3.7 Hz), 2.78 (1H, m), 2.86 (1H, dd, J=13.0, 10.1 Hz), 2.93 (1H, m), 3.02–3.09 (3H, m), 3.94 (1H, m), 4.11 (1H, m), 6.60 (1H, br s)

EXAMPLE 12

Preparation of N-tert-butyl 1-(3'-azido-2'(S)-hydroxypropyl)-4-tert-butyloxycarbonylpiperazine-2(S)-carboxamide, Compound 16

To a magnetically stirred solution of Compound 15 (4.708 g, 13.79 mmol) in isopropanol (30 mL) was added LiN₃ (1.350 g, 27.58 mmol) and the mixture was heated to 75° C. for 5 h. The mixture was cooled to room temperature and solvent removed under reduced pressure and the residue was taken up in EtOAc (100 mL) and washed with sat aq NaHCO₃ solution (50 mL) and brine (50 mL). The organic solution was dried over anhyd Na₂SO₄, filtered, and concentrated. The residue was purified on a silica gel column chromatography to give 3.661 g (69% yield) of a pale yellow oil. ¹H NMR (CDCl₃) 1.36 (9H, s), 1.46 (9H, s), 2.42 (1H, ddd, J=12.1, 8.9, 3.5 Hz), 2.52 (1H, m), 2.73 (1H, dd, J=13.3, 4.5 Hz), 2.86–2.92 (2H, m), 3.10–3.30 (2H, m), 3.29 (1H, dd, J=12.4, 6.2 Hz), 3.41 (1H, dd, J=12.6, 3.7 Hz), 3.62 (1H, m), 3.80 (1H, br d, J=11.2 Hz), 3.91 (1H, m), 6.22 (1H, m)

EXAMPLE 13

Preparation of N-tert-butyl 1-(3'-amino-2'(S)-hydroxypropyl)-4-tert-butyloxycarbonylpiperazine-2(S)-carboxamide, Compound 17

To a magnetically stirred solution of N-tert-butyl 1-(3'-azido-2'(S)-hydroxypropyl)-4-tert-butyloxycarbonylpiperazine-2(S)-carboxamide, Compound 16 (1.662 g, 4.44 mmol) in 100 mL EtOAc was added Pd on carbon (400 mg). The mixture was stirred under an atmospheric pressure of hydrogen for 18 h at ambient temperature. The mixture was filtered and the filtrate concentrated under reduced pressure. The residue was purified on a silica gel chromatography to provide 1.291 g of pale yellow solid (81% yield). ¹H NMR (CDCl₃) 1.35 (9H, s), 1.46 (9H, s), 1.80 (3H, br s), 2.35–2.44 (3H, m), 2.61 (1H, dd, J=13.2, 3.9 Hz), 2.67 (1H, m), 2.84 (1H, dd, J=8.8, 3.7 Hz), 2.90 (1H, d, J=12.6 Hz), 3.05 (2H, m), 3.14 (1H, dd, J=13.4, 8.8 Hz), 3.75 (1H, m), 3.92 (1H, dd, J=13.4, 2.4 Hz), 6.43 (1H, br s)

EXAMPLE 14

Preparation of N-tert-butyl 1-{3'-[3"-(2"'-Phenylethyl-amido)carboxy-1"(R),4"(S)-bicyclo[2.2.1]hept-5"-en-2"(R)-ylcarbonyl]amino-2'(S)-hydroxy}propyl-4-(1',1'-dimethyl)ethyloxycarbonylpiperazine-2(S)-carboxamide, Compound 18 (RR₁=H, CH₂CH₂Ph)

To a magnetically stirred solution of the Compound 12 (RR₁=H, CH₂CH₂Ph, 79.5 mg, 0.279 mmol) and Compound 17 (100 mg, 0.279 mmol) in DMF (0.65 mL) were added HOBT (37.7 mg, 0.279 mmol), EDC (53.5 mg, 0.279 mmol) and triethylamine (38.9 μL, 0.279 mmol). The mixture was stirred for 18 h at ambient temperature. The solvent was removed by rotary evaporation and the residue dissolved in EtOAc (10 mL). The EtOAc solution was washed with sat aq NaHCO₃ solution (5 mL) and brine (5 mL) and dried over anhyd Na₂SO₄. Filtration followed by concentration in vacuo provided a crude product which was purified on a silica gel column chromatography (eluted with 1.5–2.5% MeOH in CH₂Cl₂) to yield 0.125 g of a white solid (72% yield). HPLC (at 215 nm) 97.1% pure (λmax=255 nm). ¹H NMR (CDCl₃) 1.36 (9H, s), 1.45 (1H, d J=obscure), 1.46 (9H, s), 1.72 (1H, d, J=8.4 Hz), 2.32 (1H, m), 2.35 (1H, m), 2.41 (2H, m), 2.58 (1H, dd, J=13.2, 6.6 Hz), 2.80 (2H, m), 2.99–3.09 (4H, m), 3.12–3.22 (3H, m), 3.42 (1H, m), 3.53 (1H, m), 3.58 (1H, m), 3.74 (1H, d, J=12.3 Hz), 3.86 (1H, dd, J=6.2, 2.9 Hz), 3.90 (1H, d, J=13.9 Hz), 5.97 (1H, br s), 6.03 (1H, br s), 6.22 (1H, dd, J=5.3, 3.1 Hz), 6.31 (1H, br s), 7.17–7.33 (5H, m).

Analysis for C₃₄H₅₁O₆N₅.0.6 H₂O calcd: C: 64.14, H: 8.26, N: 11.00 obtained: C: 64.19, H: 8.22, N: 10.75

EXAMPLE 15

Preparation of N-tert-butyl 1-{3'-[3"-(2"'-Phenylethylamido)carboxy-1"(R),4"(S)-bicyclo[2.2.1]hept-5"-en-2"(R)-ylcarbonyl]amino-2'(S)-hydroxypropyl}piperazine-2(S)-carboxamide, Compound 19 (RR₁=H, CH₂CH₂Ph)

A solution of Compound 18 (RR₁=H, CH₂CH₂Ph) (108 mg, 0.172 mmol) in dry HCl saturated EtOAc (25 mL) was stirred at 0° C. for 30 min. Excess HCl gas was expelled by bubbling Ar through for 15 min and the solution was concentrated. The residue was dissolved in EtOAc (20 mL) and washed with 1N NaOH solution (20 mL), water (20 mL) and brine (20 mL). The organic layer was dried over anhyd MgSO₄, filtered and concentrated under reduced pressure to give 54 mg of pale brown solid. HPLC (at 215 nm) 96.2% pure (λmax=265 nm); ¹H NMR (CDCl₃) 1.36 (9H, s), 1.50 (1H, d, J=7.7 Hz), 1.73 (1H, d, J=7.7 Hz), 2.34 (1H, m), 2.49 (1H, m), 2.50–2.63 (2H, m), 2.81 (2H, m), 2.85–3.02 (6H, m), 3.07 (2H, m), 3.23 (1H, m), 3.41–3.57 (4H, m), 3.86 (1H, m), 5.98 (1H, d, J=2.6 Hz), 6.04 (1H, br s), 6.24 (1H, dd, J=6.0, 3.5 Hz), 6.84 (1H, br s), 7.18–7.36 (5H, m), 7.60 (1H, br s); HRMS (M+1)=526.3399 (calcd 526.3393)

EXAMPLE 16

Preparation of N-tert-butyl 1-{3'-[3"-(2"'-Phenylethyl-amido)carboxy-1"(R),4"(S)-bicyclo[2.2.1]hept-5"-en-2"(R)-yl]carboxyamino-2'(S)-hydroxy}propyl-4-cyclobutyl-piperazine-2(S)-carboxamide, Compound 20 (RR₁=H, CH₂CH₂Ph, R₂R₃=—(CH₂CH₂CH₂)—)

To a magnetically stirred solution of Compound 19 (19 mg, 0.0361 mmol) in dichloroethane (0.025 mL) were added cyclobutane (5.4 μL, 0.072 mmol), NaB(OAc)₃H (11.5 mg, 0.054 mmol) and acetic acid (2.5 μL, 0.043 mmol). The mixture was stirred at ambient temperature for 60 h. The mixture was diluted with EtOAc (5 mL), washed with sat aq NaHCO₃ solution (5 mL) and brine (5 mL), and dried over anhyd Na₂SO₄. The crude product was purified on a silica gel chromatographic column (0.5:3:97 NH₄OH—MeOH—CH₂Cl₂) to provide 9.7 mg (46% yield) of a white solid. HPLC (at 215 nm) 96.1% pure (λmax=336 nm), MS (FAB, M+1) 580, HRFABMS (M+1) calcd 580.3863 obsd 580.3860. $^1$H NMR (CDCl$_3$) 1.36 (1H, d, J=8.6 Hz), 1.38 (9H, s), 1.48 (1H, d, J=8.6 Hz), 1.67–1.86 (5H, m), 2.01–2.17 (3H, m), 2.29 (1H, dd, J=11.5, 2.9 Hz), 2.33 (1H, dd, J=4.8, 1.3 Hz), 2.49 (1H, dd, J=13.2, 3.5 Hz), 2.59–2.73 (5H, m), 2.80 (2H, t, J=7.1 Hz), 2.99–3.01 (3H, m), 3.14 (1H, m), 3.18 (1H, m), 3.38–3.57 (3H, m), 3.83 (1H, m), 6.03 (1H, dd, J=5.5, 2.0 Hz), 6.21 (1H, dd, J=5.7, 3.1 Hz), 6.25 (1H, br s), 6.67 (1H, br s), 7.18–7.32 (5H, m), 8.48 (1H, br s).

EXAMPLE 17

Preparation of N-tert-butyl 1-{3'-[3"-(2"'-Phenylethyl-amido)carboxy-1"(R),4"(S)-bicyclo [2.2.1]hept-5"-en-2"(R)-yl]carboxyamino-2'(S)-hydroxy}propyl-4-(2',6'-dimethyl-pyridyl) methylpiperazine-2(S)-carboxamide, Compound 21 (RR$_1$=H, CH$_2$CH$_2$Ph, Ar=4-(2,6-dimethylpyridyl))

To a magnetically stirred solution of Compound 19 (26.8 mg, 0.051 mmol) in DMF (0.5 mL) were added 4-chloromethyl-2,6-dimethylpyridine hydrochloride (14.7 mg, 0.077 mmol) and triethylamine (17.8 μL, 0.128 mmol). The mixture was stirred at ambient temperature for 18 h. The mixture was diluted with EtOAc (10 mL) and washed with sat aq NaHCO$_3$ solution (5 mL) and brine (5 mL), and dried over anhyd Na$_2$SO$_4$. The crude product was purified on a silica gel chromatographic column (eluted with 2% MeOH—CH$_2$Cl$_2$) to give 18.9 mg of a white solid (57% yield). HPLC (215 nm) 98.5% pure (λmax=269 nm), $^1$H NMR (CDCl$_3$) 1.37 (9H, s), 1.49 (1H, d, J=8.4 Hz), 1.71 (1H, d, J=8.4 Hz), 2.35 (2H, m), 2.52 (6H, s), 2.56 (1H, m), 2.53–2.65 (4H, m), 2.74 (1H, m), 2.78–83 (1H, m) 2.80 (2H, t, J=6.8 Hz), 2.98 (2H, m), 3.01 (1H, m), 3.15 (1H, m), 3.17 (1H, m), 3.39 (2H, m), 3.44 (1H, m), 3.52 (1H, m), 3.53(1H, m), 3.84 (1H, m), 6.00 (1H, d, J=4.0 Hz), 6.13 (1H, br s), 6.22 (1H, dd, J=5.3, 3.3 Hz), 6.79 (1H, br s), 6.88 (2H, s), 7.17–7.32 (5H, m), 7.61 (1H, br s)

Analysis for C$_{37}$H$_{52}$N$_6$O$_4$·0.7 EtOAc calcd: C: 67.66, H: 8.22, N: 11.89 obsd: C: 67.80, H: 8.34, N: 11.54

EXAMPLE 18

Preparation of 3-[N-(4-methylphenylsulfonyl) isobutylamino]-propane-1(RS),2-oxide, Compound 23

To a magnetically stirred solution of p-toluenesulfonyl chloride (3.813 g, 20.0 mmol) in dichloromethane (25 mL) was added a mixture of isobutylamine (2,48 mL, 25 mmol) and triethylamine (3.485 mL, 25 mmol) in dichloromethane (5 mL) at 0° C. The mixture was stirred for 3 h while warming up to room temperature. The reaction mixture was washed with 1N aq HCl solution (30 mL, then 20 mL), and sat aq NaHCO$_3$ solution (30 mL). The organic layer was dried over anhyd MgSO$_4$, filtered and concentrated by rotary evaporation. The residue was pumped overnight to give 4.304 g (18.9 mmol, 95% yield) of a white solid.

To a solution of this white solid in THF (30 mL) at −78° C. was added nBuLi (2.5M solution in hexane, 20 mmol). AT the end of addition the solution turned yellow. The mixture was stirred for 20 min and freshly distilled epichlorohydrin (2.35 mL, 30 mmol) was added dropwise. The mixture was allowed to warm to room temperature over 1 h and stirring was continued for 3 h at 23° C. Sat aq NH$_4$Cl solution (50 mL) was added to the reaction mixture and it was extracted with EtOAc (2×50 mL). The organic layer was washed with 1N HCl (2×30 mL), sat aq NaHCO$_3$ (20 mL) and brine (30 mL). It was dried over anhyd MgSO$_4$, filtered and concentrated. The residue was purified on a silica gel column chromatography (9–10% EtOAc/hexane) to give 4.00 g (75% yield) of a colorless oil. $^1$H NMR (CDCl$_3$) 0.91 (3H, d, J=6.6 Hz), 0.95 (3H, d, J=6.6 Hz), 1.97 (1H, septet, J=~7 Hz), 2.42 (3H, s), 2.50 (1H, dd, J=4.6, 2.6 Hz), 2.76 (1H, t, J=4.4 Hz), 2.87 (1H, dd, J=15.2, 7.3 Hz), 2.90 (1H, dd, J=13.4, 7.3 Hz), 3.03 (1H, m), 3.04 (1H, dd, J=13.6, 8.1 Hz), 3.57 (1H, dd, J=15.2, 3.7 Hz), 7.31 (2H, d, J=7.9 Hz), 7.70 (2H, d, J=8.4 Hz).

EXAMPLE 19

Preparation of 3-azido-1-(N-(4-methylphenylsulfonyl) isobutylamino)-2(RS)-propanol, Compound 24

To a solution of 3-[N-(4-methylphenylsulfonyl) isobutylamino]propane-1,2-oxide, Compound 23 (2.289 g, 8.077 mmol) in isopropanol was added lithium azide (0.791 g, 16.15 mmol) and the mixture was heated to 80° C. for 5 h. The solvent was removed and the residue was partitioned between water (20 mL) and EtOAc (30 mL). The aqueous layer was extracted with EtOAc (20 mL) and organic layers combined. The combined organic layers were washed with sat NaHCO$_3$ solution (20 mL) and brine (20 mL). It was dried over anhyd MgSO$_4$, filtered and concentrated by rotary evaporation to provide 2.615 g (99% yield) of a colorless oil. $^1$H NMR (CDCl$_3$) 0.90 (3H, d, J=6.6 Hz), 0.95 (3H, d, J=6.6 Hz), 1.87 (1H, m), 2.44 (3H, s), 2.85 (1H,dd, J=13.4, 6.8 Hz), 2.97–3.02 (2H, m), 3.13–3.19 (2H, m), 3.35 (1H, dd, J=12.5, 5.5 Hz), 3.40 (1H, dd, J=12.6, 4.9 Hz), 4.00 (1H, m), 7.33 (2H, d, J=8.4 Hz), 7.69 (2H, d, J=8.2 Hz).

EXAMPLE 20

Preparation of 1-amino-3-(N-(4-methylphenyl-sulfonyl)isobutylamino)-2(RS)-propanol, Compound 25

To a solution of Compound 24 (2.615 g, 8.011 mmol) in EtOH (20 mL) was added Pd(OH)$_2$/C (1.00 g). The mixture was stirred under hydrogen atmosphere for 1 day at ambient temperature. The mixture was filtered and the filtrate concentrated to yield 2.036 g (85% yield) of a colorless oil. $^1$H NMR (CDCl$_3$) 0.91 (3H, d, J=6.6 Hz), 0.91 (3H, d, J=6.6 Hz), 1.91 (1H, m), 2.43 (3H, s), 2.81 (2H, m), 2.88 (1H, dd, J=13.6, 7.3 Hz), 2.95 (1H, dd, J=12.6, 7.3 Hz), 2.99 (1H, dd, J=14.5, 7.3 Hz), 3.14 (1H, dd, J=14.8, 5.3 Hz), 3.75 (1H, m), 7.31 (2H, d, J=8.4 Hz), 7.69 (2H, J=8.4 Hz).

EXAMPLE 21

Preparation of 4-aza-1-[3'(R)-tert-butylamidocarboxyl-1'(R),4'(S)-bicyclo[2.2.1]hept-5'-en-2'(R)-ylcarbonyl]amino-2(RS)-hydroxy-6-methyl-4-(4'-methylbenzenesulfonyl)-heptane, Compound 26, (RR$_1$=H, t-Bu)

A mixture of Compound 25 (50.4 mg, 0.168 mmol), 12 (RR'=H, C(CH$_3$)$_3$, 25.3 mg, 0.107 mmol), HBT (22.2 mg, 0.164 mmol), EDC (36.1 mg, 0.188 mmol) and Et$_3$N (0.030 mL, 0.215 mmol) in DMF (1.0 mL) was stirred at ambient temperature for 2 days. Solvent was removed by rotary evaporation and the residue was dissolved in EtOAc (20 mL) and it was washed with 10% aq citric acid solution (10 mL), sat aq sodium bicarbonate solution (10 mL) and brine (10 mL). The organic layer was dried over anhyd sodium sulfate, filtered and concentrated to give a pale yellow solid. It was purified on a silica gel chromatographic column (eluted with 1% methanol-dichloromethane) to provide 31.9 mg (55% yield) of a white solid as a 1:1 mixture of diastereomers. MS (M+1)=520: HRMS (M+1)=520.2852, calcd for $C_{27}H_{42}N_3O_5S$, 520.2845: $^1H$ NMR (CDCl$_3$) 0.89 (3H, d, J=6.8 Hz), 0.91 (3H, d, J=6.6 Hz), 1.32 (9/2H, s), 1.33 (9/2H, s), 1.69 (1H, d, J=8.6 Hz), 1.89 (1H, m), 2.43 (3H, s), 2.46 (1H, m), 2.81 (1H, dd, J=13.4, 7.1 Hz), 2.89 (1H, dd, J=14.8, 6.4 Hz), 2.95 (1H, dd, J=8.1, 3.8 Hz), 2.99 (1H, m), 3.00–3.07 (2H, m), 3.17 (1/2H, dd, J=9.3, 6.2 Hz), 3.21 (1/2H, dd, J=9.5, 6.4 Hz), 3.34 (1H, m), 3.67 (1H, m), 3.92 (1H, m), 3.96 (1/2H, d, J=3.5 Hz), 4.04 (1/2H, d, J=3.3 Hz), 5.83 (1/2H, br s), 5.87 (1/2H, br s), 6.18 (1H, m), 6.29 (1H, m), 6.92 (1H, m), 7.32 (2H, d, J=8.1 Hz), 7.67 (a half of 2H, d, J=8.2 Hz), 7.69 (a half of 2H, d, J=8.2 Hz); Analysis for $C_{27}H_{41}N_3O_5S.0.4$ $CH_2Cl_2$ calcd: C: 59.44, H: 7.61, N: 7.59 found: C: 59.61, H: 7.63, N: 7.48

EXAMPLE 22

Preparation of 4-aza-1-[3'(R)-benzylamidocarboxyl-1'(R),4'(S)-bicyclo[2.2.1]hept-5'-en-2'(R)-ylcarbonyl]amino-2(RS)-hydroxy-6-methyl-4-(4'-methylbenzenesulfonyl)-heptane, Compound 26, (RR$_1$=H, CH$_2$Ph)

47% Yield, HPLC (at 215 nm) 98% pure (λmax=229 nm); MS (M+1)=554; HRMS (M+1)=554.2692, calcd for $C_{30}H_{40}N_3O_5S$, 554.2689; $^1H$ NMR (CDCl$_3$) 0.89 (3H, d, J=6.8 Hz), 0.91 (3H, d, J=8.4 Hz), 1.58 (1H, m), 1.72 (1H, d, J=8.6 Hz), 1.87 (1H, m), 2.42 (3H, s), 2.53 (1H, m), 2.81 (1H, dd, J=12.5, 7.1 Hz), 2.88 (1H, m), 2.95 (1H, m), 3.05–3.22 (3H, m), 3.34 (1H, m), 3.69 (1H, m), 3.89 (1/2H, d, J=3.5 Hz), 3.92 (1H, m), 3.97 (1/2H, d, J=3.5 Hz), 3.38 (1H, m), 4.48 (1H, m), 6.20 (1H, m), 6.30 (1H, m), 6.41 (1H, m), 6.92 (1/2H, m), 6.98 (1/2H, m), 7.24–7.36 (7H, m), 7.66 (a half of 2H, d, J=8.8 Hz), 7.68 (a half of 2H, d, J=8.6 Hz). Analysis for $C_{30}H_{39}N_3O_5S.0.60$ $H_2O$ calcd: C: 63.83, H: 7.18, N: 7.44 found: C: 63.84, H, 6.98, N: 7.42

EXAMPLE 23

Preparation of 4-aza-1-[3'(R)-(2"-phenylethylamido)carboxyl-1'(R),4'(S)-bicyclo[2.2.1]hept-5'-en-2'(R)-ylcarbonyl]amino-2(RS)-hydroxy-6-methyl-4-(4'-methylbenzenesulfonyl)heptane, Compound 26, (RR$_1$=H, CH$_2$CH$_2$Ph)

55% yield; MS (M+1)=568; HRMS (M+1)=568.2841, calcd for $C_{31}H_{42}N_3O_5S$=568.2845; UV λmax=229 nm; $^1H$ NMR (CDCl$_3$) 0.89 (3H, d, J=7.1 Hz), 0.91 (3H, d, J=8.1 Hz), 1.21 (1H, t, J=7.0 Hz), 1.68 (1H, d, J=8.6 Hz), 1.88 (1H, m), 2.42 (1H, m), 2.43 (3H, s), 2.82 (2H, m), 2.87 (1H, m), 2.96 (1H, m), 2.98 (2H<m), 3.04 (1H, m), 3.19 (1H, m), 3.33 (1H, m), 3.45 (1H, m), 3.54 (1H, m), 3.66 (1H, m), 3.91 (1H, m), 3.90 (1/2H, d, J=3.4 Hz), 3.99 (1/2H, d, J=3.3 Hz), 6.01 (2H, m), 6.24 (1H, m), 6.95 (1H, m), 7.28–7.32 (7H, m), 7.66 (a half of 2H, d, J=8.2 Hz), 6.69 (a half of 2H, d, J=8.2 Hz);

Analysis for $C_{31}H_{41}N_3O_5S.0.75$ $H_2O$ calcd: C; 64.06, H: 7.37, N: 7.23 found: C: 64.02, H: 7.13, N: 7.16

EXAMPLE 24

Preparation of 4-aza-1-[3'(R)-(N',N'-bisphenylmethyl-amido)carboxyl-1'(R),4'(S)-bicyclo[2.2.1]hept-5'-en-2'(R)-ylcarbonyl]amino-2(RS)-hydroxy-6-methyl-4-(4'-methyl-benzenesulfonyl) heptane, Compound 26, (RR$_1$=(CH$_2$Ph)$_2$)

23% yield; UV (λmax) 225 nm; MS (M+1)=644; HRMS (M+1)=644.3151, calcd for $C_{37}H_{46}N_3O_5S$ 644.3158; $^1H$ NMR (CDCl$_3$) 0.88 (3H, d, J=6.6 Hz), 0.91 (1H, d, J=6.4 Hz), 1.26 (1H, t, J=7.1 Hz), 1.44 (1H, m), 2.76–2.91 (2H, m), 2.93–3.02 (2H, m), 3.07 (1H<m), 3.16–3.24 (1.5H, m), 3.33 (0.5H, m), 3.58–3.72 (2H, m), 3.78 (1H, m), 3.93 (0.5H, d, J=3.4 Hz), 4.08 (0.5H, d, J=3.3 Hz), 4.30 (1H, d, J=14.8 Hz), 4.52 (1H, d, J=16.9 Hz), 4.72–4.80 (2H, m), 6.11 (1H, dd, J=5.7, 2.9 Hz), 6.41 (1H, dd, J=5.5, 2.9 Hz), 7.14–7.39 (12H, m), 7.67 (a half of 2H, d, J=8.2 Hz), 7.68 (a half of 2H, d, J=8.2 Hz);

Analysis for $C_{37}H_{45}N_3O_5S.0.95$ $H_2O$ calcd: C: 67.24, H: 7.15, N: 6.36 found: C: 66.92, H: 6.91, N: 6.07

EXAMPLE 25

Preparation of N-1'(S)-(2'(R)-hydroxyindanyl) 5-amino-3(S)-hydroxy-2(R)-phenylmethylpetanamide, Compound 30

A mixture of Compound 27 (3.77 g, 10 mmol) and lithium azide (4.90 g, 100 mmol) in iPrOH (50 mL) was heated to 80° C. for 15 h. The mixture was cooled to room temperature and solvent removed. The residue was taken up in EtOAc (100 mL) and washed with sat aq NaHCO$_3$ solution (100 mL) and brine (100 mL). The organic layer was dried over anhyd Na$_2$SO$_4$ and filtered. The filtrate was concentrated by rotary evaporation to give crude product of Compound 28. This crude product was then taken up in EtOAc (100 mL) and Pd(OH)$_2$/C (0.8 g) was added. The mixture was stirred under hydrogen atmosphere for 18 h at room temperature. Solids were filtered over Celite® and the filtrate was concentrated to furnish crude Compound 29. A solution of Compound 29 (0.95 g, 2.41 mmol) in HCl gas saturated EtOAc (45 mL) was stirred at 0° C. for 30 min. Excess HCl gas was removed by bubbling Ar through and the mixture was concentrated by rotary evaporation. The residue was dissolved in EtOAc (30 mL) and washed with aq 1N NaOH solution (20 mL). The aqueous layer was extracted with EtOAc (4×10 mL) and organic layers combined. Combined organic layers were dried over anhyd Na$_2$SO$_4$, filtered and concentrated under reduced pressure to provide 0.915 g of crude product. Column chromatography (silica gel, 4–4.75% MeOH/methylene chloride) provided pure product, 0.16 g, 19% yield. $^1H$ NMR (CDCl$_3$) 1.61 (1H, m), 1.97 (1H, m), 2.53 (1H, dd, J=12.6, 8.4 Hz), 2.79–2.97 (5H, m), 3.02 (1H, dd, J=16.7, 5.3 Hz), 3.63 (1H, m), 4.23 (1H, m), 5.29 (1H, dd, J=8.6, 4.8 Hz), 5.93 (1H, d, J=8.6 Hz), 7.10–7.34 (10H, m).

EXAMPLE 26

Preparation of N-1'(S)-(2'(R)-hydroxyindanyl) 5-[3'-(2"-Phenylethylamido)carboxy-1'(R),4'(S)-bicyclo[2.2.1]hept-5'-en-2'(R)-yl]carboxyamino-3(S)-hydroxy-2(R)-phenylmethylpetanamide, Compound 31 (RR'=H, CH$_2$CH$_2$Ph)

A mixture of N-2'-Phenylethylamidocarboxy-1(R),4(S)-bicyclo[2.2.1]hept-5-en-2(R)-yl carboxylic acid, Compound 12 (32.2 mg, 0.113 mmol), N-1(S)-(2(R)-hydroxyindanyl) 5-amino-3(S)-hydroxy-2(R)-phenylmethylpetanamide, Compound 30 (40 mg, 0.113 mmol), HOBT (15.3 mg, 0.113 mg), EDC (21.6 mg, 0.113 mmol) and triethylamine (15.7 µL, 0.113 mmol) in DMF (0.5 mL) was stirred at ambient temperature for 15 h. Solvent was removed by rotary evaporation and the residue was taken up in EtOAc (10 mL) and washed with sat aq NaHCO$_3$ (5 mL) and brine (5 mL). The organic solution was dried over anhyd Na$_2$SO$_4$, filtered and concentrated by rotary evaporation. The residue was purified by silica gel chromatography (eluted with 2.5–2.75% MeOH—CH$_2$Cl$_2$) to give 27.3 mg of a white solid (39% yield). mp 188°–190° C., MS (M+1) 622, HRFABMS (M+1) calcd 622.3281 obsd 622.3287. $^1$H NMR (CD$_3$OD) 1.33 (1H, d, J=8.5 Hz), 1.52 (1H, t, J=7.5 Hz), 1.77 (1H, d, J=8.1 Hz), 1.93 (1H, t, J=9.0 Hz), 2.49 (1H, d, J=4.8 Hz), 2.74–3.08 (9H, m), 2.91–3.08 (5H, m), 3.17–3.23 (3H, m), 3.28 (1H, m), 3.31 (1H, m), 3.45 (1H, m), 3.79 (1H, m), 4.32 (1H, m), 5.23 (1H, d, J=4.8 Hz), 5.89 (1H, br s), 6.22 (1H, m), 7.18–7.27 (14H, m), 7.80 (1H, br s)

EXAMPLE 27

Preparation of N-1'(S)-(2'(R)-hydroxyindanyl) 5-[3'-tert-butylamido-carboxy-1'(R),4'(S)-bicyclo [2.2.1] hept-5'-en-2'(R)-ylcarbonyl]amino-3(S)-hydroxy-2 (R)-phenyl-methylpetanamide, Compound 31 (RR'=H, C(CH$_3$)$_3$)

mp 187°–190° C., HPLC (at 215 nm) 97.2% pure (1max= 261 nm), 1.32 (9H, s), 1.54 (1H, d, J=8.2 Hz), 1.65 (1H, dd, J=11.0, 10.4 Hz), 1.73 (1H, d, J=8.2 Hz), 1.84 (1H, br s), 1.90 (1H, dd, J=13, 11.4 Hz), 2.41 (1H, d, J=4.0 Hz), 2.79–3.04 (8H, m), 3.22 (1H, dd, J=12.1, 5.5 Hz), 3.40 (1H, dd, J=10.3, 2.8 Hz), 3.85 (1H, br s), 4.25 (1H, br s), 4.30 (1H, br s), 5.27 (1H<dd, J=7.9, 4.8 Hz), 5.68 (1H, s), 6.11 (1H, s), 6.15 (1H, d, J=8.4 Hz), 6.28 (1H, s), 7.01 (1H., br s), 7.12–7.30 (9H, m)

Analysis for C$_{34}$H$_{43}$N$_3$O$_5$.1.2 H$_2$O calcd: C: 68.59, H: 7.69, N: 7.06, obsd: C: 68.64, H: 7.40, N: 7.00

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A compound of the formula

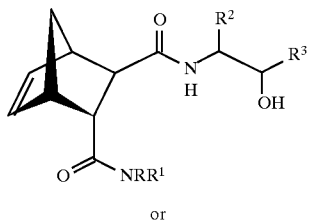

I or

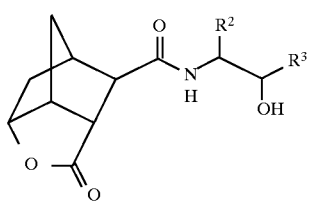

R and R$^1$ are independently
a) hydrogen, or
b) —C$_{1-4}$alkyl unsubstituted or substituted with one or more of
i) halo,
ii) hydroxy,
iii) C$_{1-3}$ alkoxy,
iv) aryl unsubstituted or substituted with one or more of C$_{1-4}$alkyl, C$_{1-4}$alkoxy, nitro, amino, amido, carboxy, hydroxy, halo or aryl;
v) —W-aryl or W-benzyl, wherein W is —O—, —S—, or —NH—; or
vii) heterocycle, unsubstituted or substituted with one or more of C$_{1-4}$alkyl, hydroxy or halo;
viii) carboxyl;
c) —C$_{3-5}$cycloalkyl, unsubstituted or substituted at the 3-position with C$_{1-4}$alkyl;
d) aryl unsubstituted or substituted with halo, C$_{1-4}$ alkyl unsubstituted or substituted one or more times with hydroxy; or
e) R and R$^1$ are joined together to form a 4–6 membered cycloalkyl or a heterocycle; and R$^2$ is
a) hydrogen;
b) Phenyl unsubstituted or substituted with one or more of —OH or C$_{1-3}$ alkoxy;
c) C$_{5-7}$cycloalkyl, unsubstituted or substituted with one or more of —OH or C$_{1-3}$alkoxy; or
d) C$_{1-4}$alkyl; and R$^3$ is —CH$_2$NR$^5$R$^6$, or

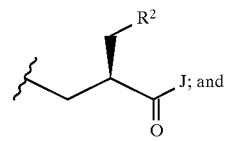

and

R$^4$ is
a) a 5- to 7-membered heterocycle, which heterocycle is unsubstituted or substituted with one or more of —C$_{1-4}$alkyl, oxo, amino or halo;
b) aryl unsubstituted or substituted with one or more of —C$_{1-4}$alkyl, C$_{1-4}$ alkoxy, nitro, oxo, amino, amido, carboxy, hydroxy, halo, or aryl;
c) C$_{1-4}$alkyl, unsubstituted or substituted once with aryl or 5- to 7-membered heterocycle; or
d) C$_{3-5}$cycloalkyl, unsubstituted or substituted at the 3-position with C$_{1-4}$alkyl; and R$^5$ is
a) —V—R$^4$; wherein V is —C(O)—Q—, or —SO$_2$— Q—, wherein Q is absent, —O—, or —NH—; and R$^6$ is
a) hydrogen, or
b) —C$_{1-4}$alkyl unsubstituted or substituted with one or more of
i) halo,
ii) hydroxy,
iii) C$_{1-3}$alkoxy,
iv) aryl unsubstituted or substituted with one or more of C$_{1-4}$alkyl, C$_{1-4}$alkoxy, nitro, amino, amido, carboxy, hydroxy, halo or aryl;
v) —W-aryl or W-benzyl, wherein W is —O—, —S—, or —NH—; or
vi) heterocycle, unsubstituted or substituted with one or more of C$_{1-4}$alkyl, hydroxy or halo;
vii) carboxyl;
c) —C$_{3-5}$cycloalkyl, unsubstituted or substituted at the 3-position with C$_{1-4}$alkyl; or
d) aryl unsubstituted or substituted with one or more of C$_{1-4}$alkyl, C$_{1-4}$alkoxy, nitro, amino, amido, carboxy, hydroxy, halo or aryl; and J is

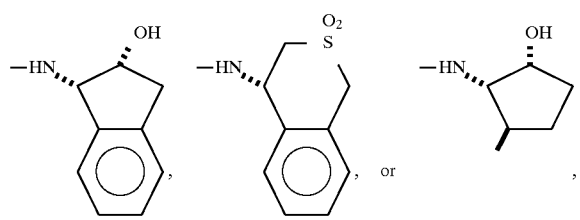

or pharmaceutically acceptable salts thereof.

2. The compound of claim 1 of the structure

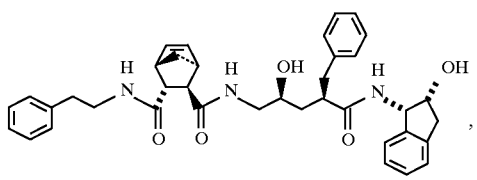

or pharmaceutically acceptable salts thereof.

3. The compound of claim 1 of the structure

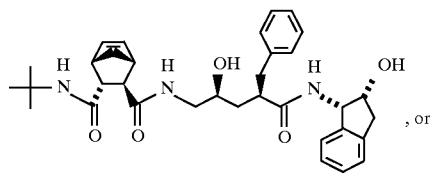

or pharmaceutically acceptable salts thereof.

4. The compound of claim 1 of the structure

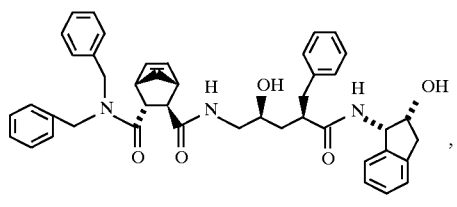

or pharmaceutically acceptable salt thereof.

5. A pharmaceutical composition comprising the compound of claim 1, and a pharmaceutically acceptable carrier.

6. The pharmaceutical composition of claim 5, in the treatment of and the delaying of the onset of AIDS, in the treatment of infection by HIV, or in the inhibition of HIV protease.

7. A method of treating and delaying the onset of AIDS, comprising administering to a mammal in need of such treatment an effective amount of a compound of claim 1.

8. A method of treating infection by HIV, comprising administering to a mammal in need of such treatment an effective amount of a compound of claim 1.

9. A method of inhibiting HIV protease, comprising administering to a mammal in need of such treatment an effective amount of a compound of claim 1.

* * * * *